(12) United States Patent
Skotton

(10) Patent No.: US 6,464,725 B2
(45) Date of Patent: Oct. 15, 2002

(54) TWO-LENS ADJUSTABLE INTRAOCULAR LENS SYSTEM

(76) Inventor: Berndt Christian Skotton, 273 Mather St., Piedmont, CA (US) 94611-5154

(*) Notice: Subject to any disclaimer, the term of this patent is extended or adjusted under 35 U.S.C. 154(b) by 6 days.

(21) Appl. No.: 09/768,876

(22) Filed: Jan. 23, 2001

(65) Prior Publication Data

US 2002/0143395 A1 Oct. 3, 2002

(51) Int. Cl.⁷ .................................................. A61F 2/16
(52) U.S. Cl. ...................... 623/6.34; 623/6.37; 623/6.32
(58) Field of Search ............................. 623/6.34, 6.37, 623/6.39, 6.32

(56) References Cited

U.S. PATENT DOCUMENTS

| | | |
|---|---|---|
| 4,074,368 A | 2/1978 | Levy et al. |
| 4,254,509 A | 3/1981 | Tennant |
| 4,409,691 A | 10/1983 | Levy |
| 4,666,446 A | 5/1987 | Koziol et al. |
| 4,892,543 A | 1/1990 | Turley |
| 4,994,082 A | 2/1991 | Richards et al. |
| 5,030,231 A | 7/1991 | Portney |
| 5,074,875 A | 12/1991 | Donn et al. |
| 5,196,028 A | 3/1993 | Portney et al. |
| 5,275,623 A | 1/1994 | Sarfarazi |
| 5,354,335 A | 10/1994 | Lipshitz et al. |
| 5,391,202 A | 2/1995 | Lipshitz |
| 5,562,731 A * | 10/1996 | Cumming .................. 623/6.34 |
| 5,876,442 A * | 3/1999 | Lipshitz et al. ............ 623/6.34 |
| 5,928,283 A | 7/1999 | Gross et al. |
| 6,117,171 A * | 9/2000 | Skottun ..................... 623/6.34 |

OTHER PUBLICATIONS

Thornton, S.P. (1986) Lens implantation with restored accommodation. Current Canadian Ophthalmic Practice. vol. 4[2].

Hara, T., et al. (1990) Accommodative intraocular lens with spring action. Part 1. Ophthalmic Surgery, vol. 21 [2] pp. 128–133.

Hara, T., et al (1992) Accommodative intraocular lens intraocular lens with spring action. Part 2. Ophthalmic Surgery, vol. 23 [9] pp. 632–635.

* cited by examiner

Primary Examiner—Dinh X. Nguyen

(57) ABSTRACT

A lens system for implantation in a human eye which makes it possible to restore accommodation. The lens system comprises one anterior lens (2) and a posterior lens (4), out of these two lenses one has positive and the other has negative lens power. Accommodation is achieved by varying the distance between the two lenses. This lens system can be made so as to generate large changes in optical power for small changes in position. It also allows the amount of change in optical power for any given amount of change in distance between the lenses to be selected relatively independently of the optical power of the overall lens system.

9 Claims, 5 Drawing Sheets

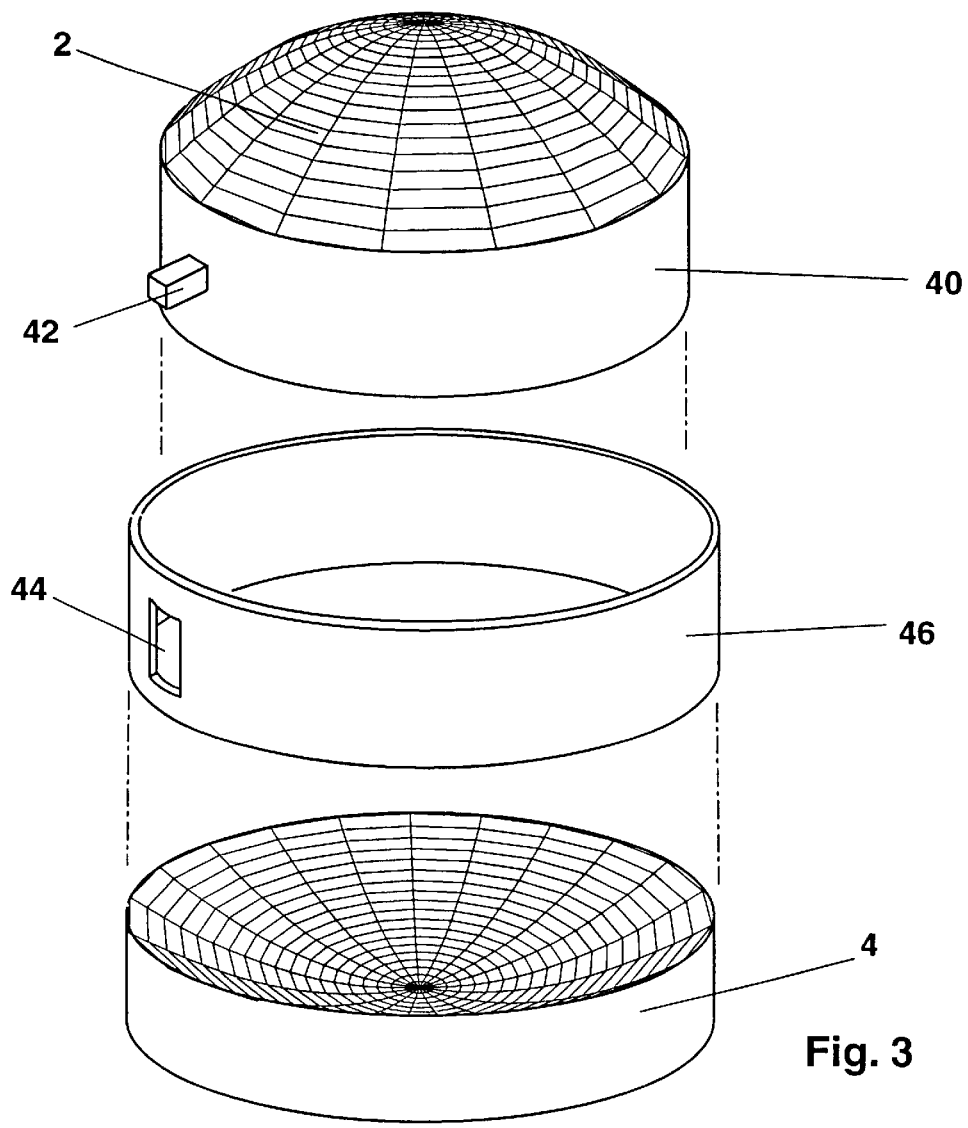
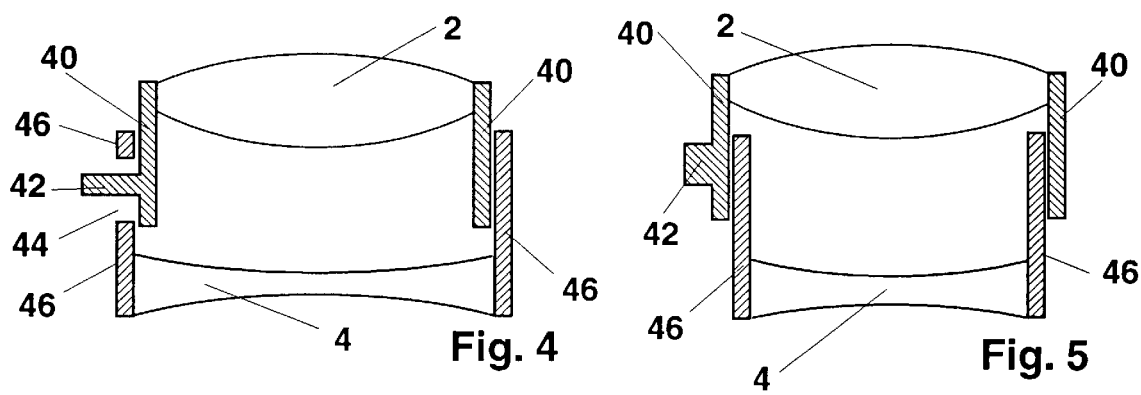
Fig. 3
Fig. 4   Fig. 5

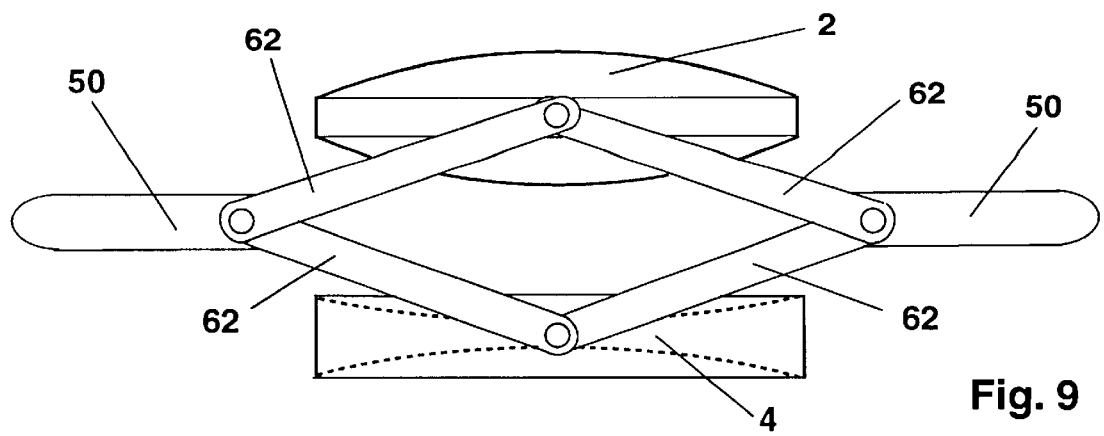
Fig. 9
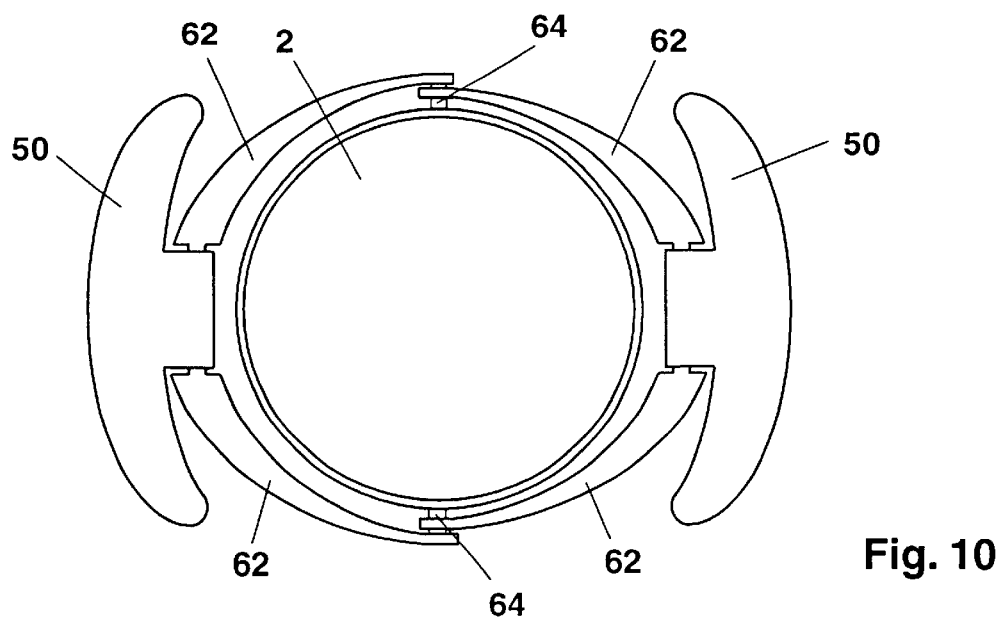
Fig. 10
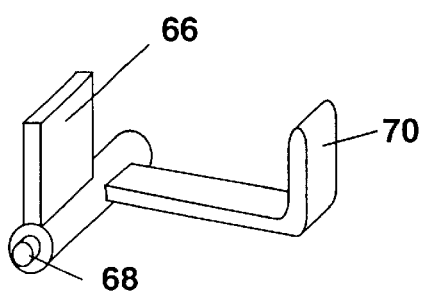
Fig. 11
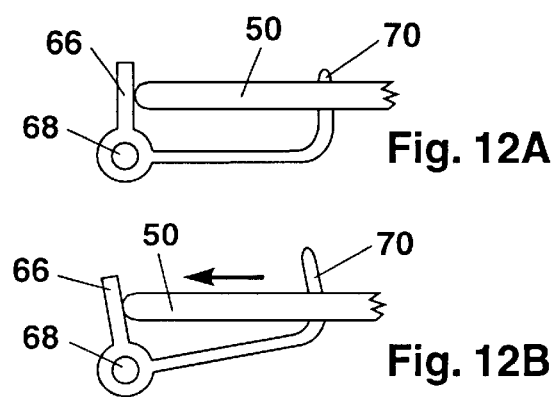
Fig. 12A
Fig. 12B

TWO-LENS ADJUSTABLE INTRAOCULAR LENS SYSTEM

BACKGROUND—Field of Invention

This invention relates to intraocular lenses, specifically to such intraocular lenses as can be used to restore accommodation.

BACKGROUND—Description of Prior Art

Several different attempts have been made to make intraocular lenses that give a patient the ability to accommodate. These attempts may be divided into two categories: those which rely on changing the shape of optical elements, and those which rely on changing the position of one or more optical elements. In the second case, changes in power are brought about by making the intraocular lens or one component of this lens move back and forth along the optical axis. Such displacements change the overall optical power of the eye and may allow a patient to adjust his or her focus so as to create sharp retinal images of objects over a range of distances.

Given the optical power of the cornea, an artificial intraocular lens will need to have a power of about 20 diopters in order to create sharp images on the retina. Such a lens will have to make rather large shifts in position in order to create a substantial accommodative range. It is not clear that the limited forces of the ciliary muscle, the limited movement of the zonules, and the limited amount of tension which can be exerted by a lens capsule (which may have been more or less damaged as a result of lens extraction) will be able to provide ample movement to result in a sufficiently large accommodative range.

Some accommodating intraocular lens designs have called for dividing the intraocular lens into two parts and altering the distance between the two parts in order to generate the changes in lens power. This design only tends to increase the problem of providing sufficient change in lens power. The reason is that if the lens is divided into two approximately equal parts only one of the two parts will in practice be free to move; the part of the lens adjacent to the vitreous body will be very much restricted from moving in a posterior direction. Thus, the available movement will be in the anterior part of the lens system. Since the anterior part of the system contains only part of the overall lens power, the anterior part will have to move farther than had all the lens power been in the moving part of the lens system.

There are two reasons why having to rely on large movements of an intraocular lens is a distinct disadvantage. First, there simply is not very much room available for a lens, or part of a lens system, to move inside the emptied lens capsule. Given that movement toward the posterior of the eye (i.e., toward the retina) is limited by the vitreous, all or most of the movement will have to be in the anterior direction (i.e., toward the cornea). Any large displacement anteriorly could bring the lens into direct physical contact with the posterior side of the iris. Such contact could damage the iris. A situation in which an artificial lens comes into direct contact with the iris should therefore be avoided. Second, both the forces and the displacements which can be effected by changes in tension of the ciliary muscle are very small. One could in theory achieve large displacements by employing a lever or a system of levers; however, because a system which amplifies the amount of movement (i.e., the distance travelled) reduces the amount of force that can be exerted, any amplification of displacement will come at the expense of a reduction in force. Thus, a system which increases the range of movement will attenuate the force which can be exerted. Given that the available force is very small to start with, a system which diminishes that force would be undesirable.

The problem facing the designer of a effective accommodating intraocular lens is to create an implantable lens, or lens system, which has the ability to transform small positional changes into large changes in lens power while at the same time has a net average power of about 20 diopters. The ability to transform small positional changes, or the application of small changes in force, into large optical changes may be referred to as "high gain". Thus, the goal is to obtain high gain for a particular amount of lens power. Ideally, when designing the intraocular lens one would like to be able to determine the gain and the overall power independently of each other.

ADVANTAGES

The main advantages of the present invention are: (a) to provide an intraocular lens system which has high gain, i.e. has the ability to translate small positional changes into large changes in optical power. (b) to allow the designer to be able to select the gain independently of the optical power. (c) to allow changes in the tension in the ciliary body to be transmitted to the intraocular lens, where these changes then can be translated into changes in optical power, without having to rely on very complicated or intricate mechanisms.

Additional advantages and objectives will become apparent from a consideration of the ensuing description and drawings.

Drawing—Figures

FIG. 3 shows an exploded view of one embodiment of the present invention, in which a skirt has been attached to the anterior lens and a cylindrical ring has been attached to the posterior lens.

FIG. 4 shows a cross section through the lens system shown in FIG. 3.

FIG. 5 shows a cross section through a lens system similar to the one in FIG. 3, but which has been modified so that the cylindrical ring fits inside the skirt.

FIG. 9 shows a side view of an embodiment of the invention, in which the separation between the anterior and the posterior lens is altered by having movement of the haptics alter the angle of elongated members.

FIG. 10 shows a frontal view of the intraocular lens shown in FIG. 9.

FIG. 11 shows a three-dimensional drawing of a part for transforming movement in a plane perpendicular to the optical axis into movement along the optical axis.

FIGS. 12A and 12B show the rotation of the part shown in FIG. 11 as it is being acted upon by one haptic.

Figure 1A:
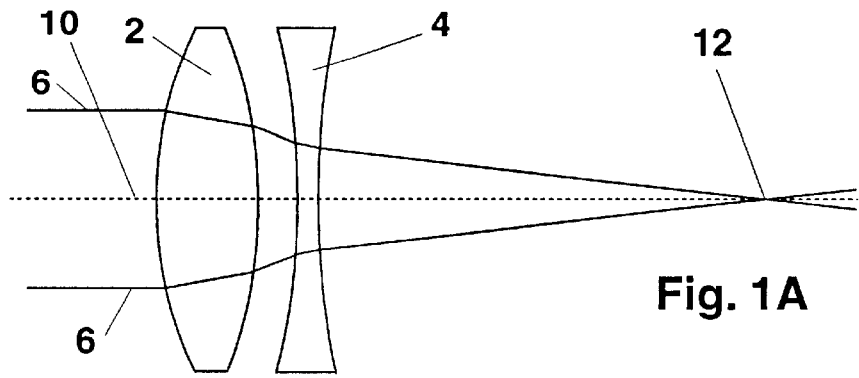
FIGS. 1A and 1B illustrate schematically in cross section the basic principle of the two-lens accommodating intraocular lens system.

| Reference Numerals In Drawings | |
|---|---|
| 2 anterior lens | 4 posterior lens |
| 6 optical ray | 10 optical axis |
| 12 focal point | 20 lens capsule |
| 22 cornea | 24 iris |
| 26 anterior chamber | 28 zonules |
| 30 ciliary body | 32 vitreous body |
| 34 conjunctiva | 36 sclera |
| 40 skirt | 42 tab |
| 44 slot | 46 cylindrical ring |
| 48 wedge | 50 haptic |
| 52 anterior ring | 54 posterior ring |
| 56 resilient element | 60 pivot |
| 62 member | 64 rod |
| 66 plate | 68 shaft |
| 70 lever | 72 resilient membrane |
| 74 liquid filled space | |

SUMMARY

A lens system for use in an accommodating intraocular lens. The lens system consists of at least two lenses. Accommodation is achieved by varying the distance between the two lenses. One of the two lenses has positive power and the other has negative power.

DESCRIPTION

Figure 1B:
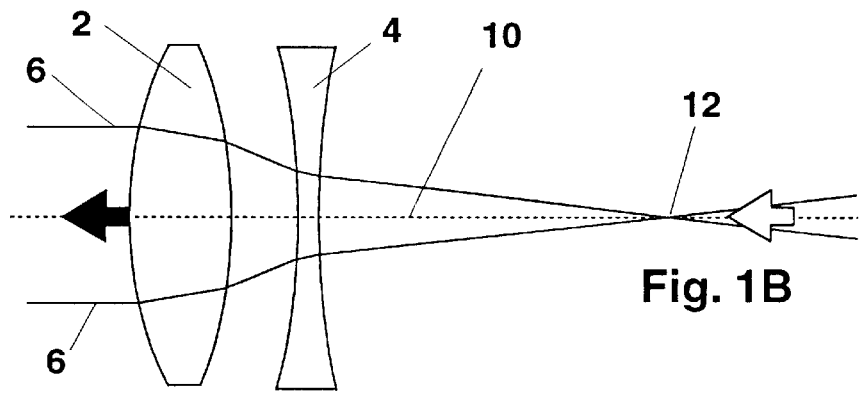

The basic principle behind the two-lens accommodating intraocular lens system is illustrated in FIG. 1A and FIG. 1B. In its most basic embodiment the lens system comprises an anterior lens 2 and a posterior lens 4. In the preferred embodiment anterior lens 2 has positive lens power and posterior lens 4 has negative lens power. Anterior lens 2 is accordingly shown as biconvex while posterior lens 4 is shown as biconcave. In FIG. 1A and FIG. 1B it can be seen that an optical ray 6 marking the path taken by a ray of light travelling trough the system from left to right first encounters anterior lens 2 where it undergoes refraction at both the anterior and posterior surfaces of this lens. This refraction bends the light toward the optical axis 10 of the lens system. After leaving the posterior surface of anterior lens 2 the light travels some small distance before entering posterior lens 4 where the optical ray is refracted outward so as to make the focal length of the lens system longer than the focal length of anterior lens 2 alone.

FIG. 1A shows optical rays 6 when the distance between anterior lens 2 and posterior lens 4 is relatively small. This causes optical rays 6 to come to a well-defined focal point 12 at some distance from the lens system. In FIG. 1B anterior lens 2 has been shifted forward, as is indicated by the filled arrow. This causes focal point 12 to move forward, as is indicated by the open arrow.

Figure 2:
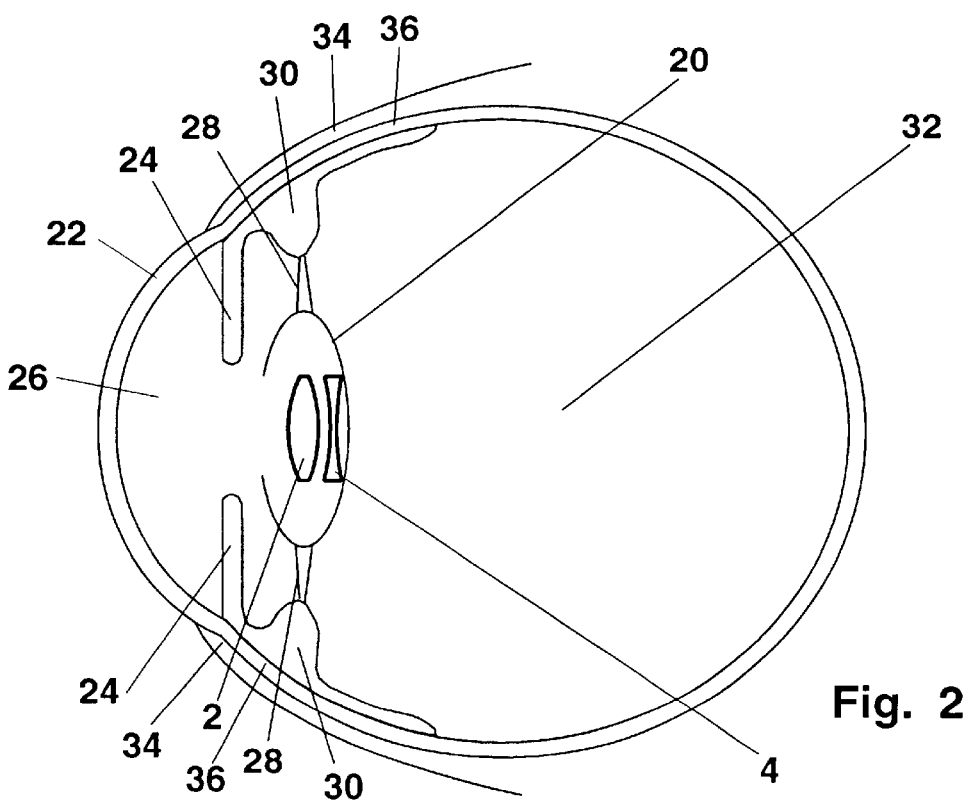
FIG. 2 shows the placement of the lens system in the emptied lens capsule.

In FIG. 2 is shown the two-lens intraocular lens system placed in its appropriate place inside the emptied lens capsule 20 of an eye. Also shown in FIG. 2 are the most prominent features of the eye: cornea 22, iris 24, anterior chamber 26, zonules 28, ciliary body 30, vitreous body 32, conjunctiva 34 and sclera 36. As can be seen, posterior lens 4 is placed so as be in close proximity to the posterior part of lens capsule 20. Posterior lens 4 may actually be in physical contact with the posterior part of lens capsule 20. Irrespective of whether or not posterior lens 4 actually rests against capsule 20, it is envisioned that posterior lens 4 will remain substantially stationary during accommodation and that the main movement will be with regard to anterior lens 2.

In FIG. 3 is shown an exploded view of one embodiment of the present lens system. In this embodiment a skirt 40 has been attached to anterior lens 2. To posterior lens 4 has been attached a cylindrical ring 46. Skirt 40 and cylindrical ring 46 have relative dimensions so that skirt 40 can fit inside of cylindrical ring 46. The purpose of skirt 40 and ring 46 is to ensure that anterior lens 2 and posterior lens 4 remain properly aligned as they move relative to each other.

In order to effect movement of skirt 40 relative to cylindrical ring 46 a slot 44 has been cut in cylindrical ring 46 and a tab 42 has been attached to skirt 40. Tab 42 is placed in such a manner that it protrudes through slot 44. In FIG. 3 only one tab 42 and one slot 44 are shown. In practice it may be appropriate for the lens system to have two or more tabs 42 and slots 44.

In FIG. 4 is shown a cross section through the lens system shown in FIG. 3 with the parts in their appropriate positions relative to each other. In FIG. 5 is shown a variant of the lens-system shown in FIGS. 3 and 4 in which skirt 40 has a larger diameter than cylindrical ring 46 so that cylindrical ring 46 fits inside skirt 40.

Figure 6:
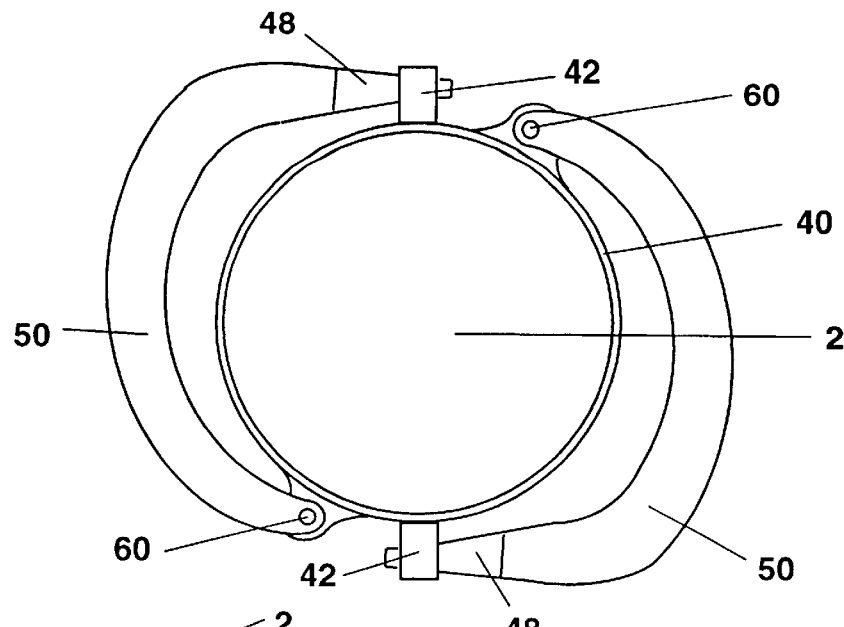
FIG. 6 shows a frontal view of an intraocular lens, including haptics, of the same embodiment as was shown in FIG. 3.
Figure 7:
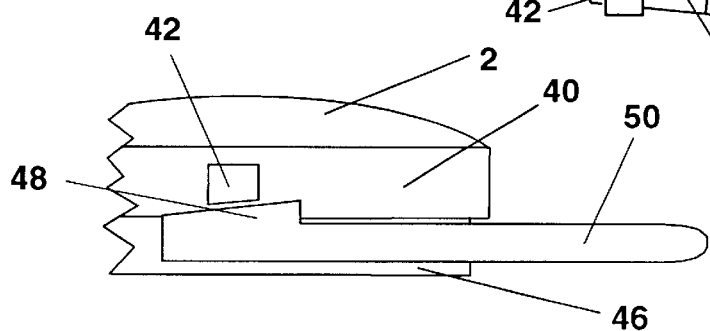
FIG. 7 shows a side view of part of the intraocular lens shown in FIG. 6.

FIG. 6 shows a frontal view of an intraocular lens based on the embodiment shown in FIG. 5. The intraocular lens includes the lens system and a pair of haptics 50. Each haptic 50 is attached to cylindrical ring 46 at a pivot 60. At the other end, each haptic 50 is shaped into a wedge 48. Each wedge 48 makes contact with tab 42 which is attached to skirt 40. The relationship between wedge 58 and tab 42 are shown in a side view in FIG. 7. Wedge 58 and tab 42 are arranged in such a manner so as to cause compression of haptics 50, that is to say movement of haptics 50 toward each other, to push skirt 40 and cylindrical ring 46 apart. Because anterior lens 2 and posterior lens 4 are, respectively, attached to skirt 40 and cylindrical ring 46, compression of haptics 50 causes the separation between anterior lens 2 and posterior lens 4 to increase.

Figure 8A:
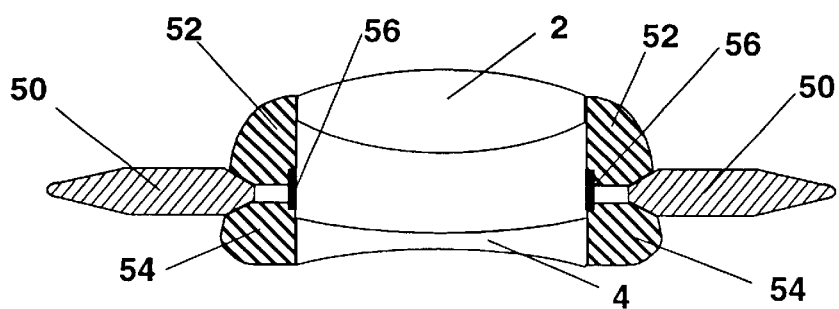
FIGS. 8A and 8B show a cross section through a second embodiment of the present invention, in which compression of the haptics force the anterior lens and the posterior lens apart.
Figure 8B:
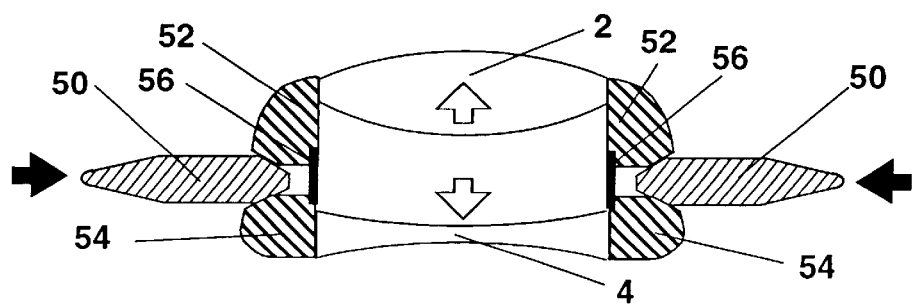

In FIGS. 8A and 8B is shown an alternative embodiment of the present invention. In this case anterior lens 2 is firmly attached to a surrounding anterior ring 52 and posterior lens 4 is attached to a surrounding posterior ring 54. Some portions of the posterior side of anterior ring 52 and the anterior side of posterior ring 54 have been bevelled. Parts of haptics 50 fit within the space separating anterior ring 52 and posterior ring 54. The part of each haptic 50 which is located within the space between anterior ring 52 and posterior ring 54 has been given a bevelled shape.

In FIG. 8A is shown a cross section through the whole intraocular lens when no pressure is being applied onto haptics 50. In FIG. 8B is shown the intraocular lens after haptics 50 have been compressed. The displacements of haptics 50 are indicated with filled arrows in FIG. 8B. Compression of haptics 50 makes wedges 48 cause anterior lens 2 and posterior lens 4 to be pushed apart. This is indicated with open arrows in FIG. 8B. When the pressure on haptics 50 is released the resilient elements 56 causes anterior ring 52 and posterior ring 54 to move toward each other.

A further embodiment of the present invention is shown in FIGS. 9 and 10. In this embodiment each of two haptics 50 makes contact with two members 62. Each member is attached to one haptic 50 in one end and to a rod 64 at the other end. Each member 62 is free to rotate around the place where it is connected to haptic 50 and around rod 64. Rod 64 in turn is attached to anterior lens 2 or posterior lens 4. The connection is such that when haptics 50 are displaced toward each other, members 62 will push anterior lens 2 and posterior lens 4 apart. FIG. 9 shows a side view of this embodiment, and FIG. 10 shows this embodiment in a frontal view.

A further embodiment of the present invention utilizes a lever system to adjust the separation between anterior lens 2 and posterior lens 4. FIGS. 11, 12A and 12B show different views of a part which is designed so at to translate movement of haptics 50 in a direction perpendicular to the optical axis 10 into movement along optical axis 10. This part is shown in a three-dimensional view in FIG. 11. It consists of a plate 66 and a lever 70. Lever 70 has an initial horizontal part and an outer vertical segment. The whole ensemble of plate 66 and lever 70 is arranged so as be able to rotate around a shaft 68.

In FIGS. 12A and 12B are shown side views of plate 66 and lever 70 as they are being acted upon by movement of haptic 50. FIG. 12A shows the situation where there is no pressure applied by haptic 50. FIG. 12B shows the situation after force has been applied to haptic 50 so as to displace haptic 50 toward the left, as indicated by the arrow. This movement causes plate 66 and lever 70 to both be tilted counterclockwise. That is to say, horizontal movement of haptic 50 is translated into vertical movement of lever 70.

Figure 13:
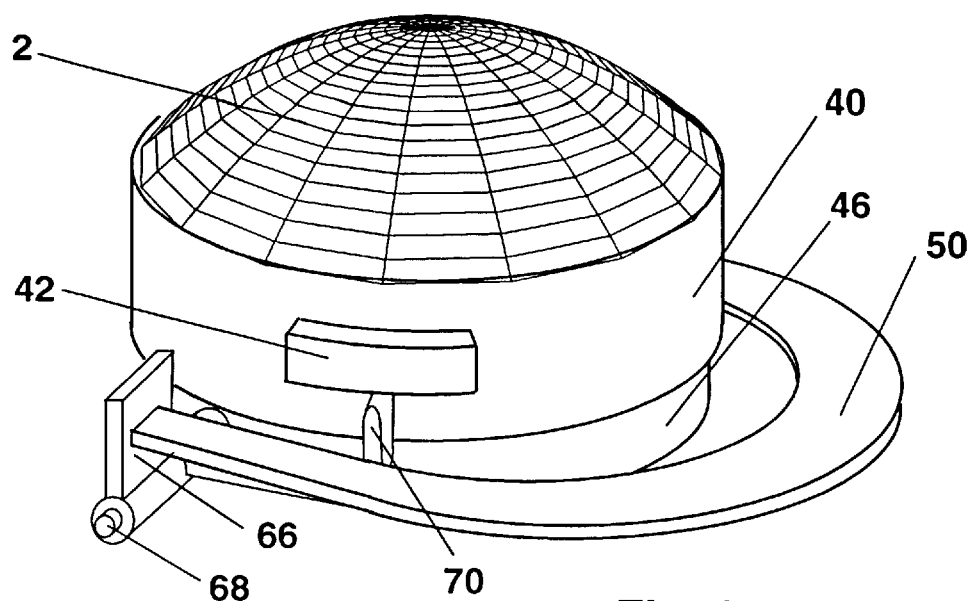
FIG. 13 shows a three-dimensional drawing of an intraocular lens illustrating the placement of one haptic and of the part shown in FIGS. 11, 12A and 12B.

In FIG. 13 is shown a three-dimensional drawing of an intraocular lens based on the use of a lever. In this case lever 70 acts on tab 42. Tab 42 is attached to skirt 40 which in turn is attached to anterior lens 2. When lever 70 moves upward it pushes upward on tab 42 causing skirt 40 and with it anterior lens 2 upward. This causes the separation between anterior lens 2 and posterior lens 4 to increase.

Figure 14A:
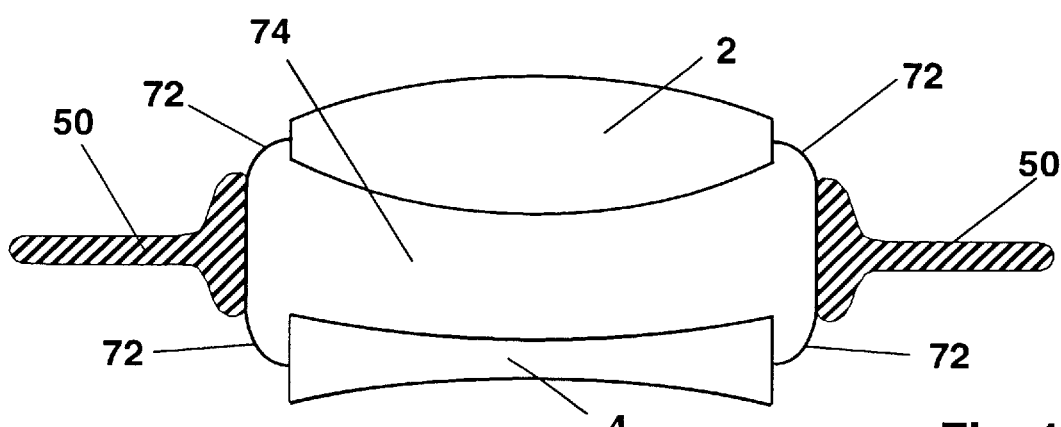
FIGS. 14A and 14B show a fourth embodiment of the present invention, in which the anterior and posterior lenses are separated by a changeable liquid-filled space.
Figure 14B:
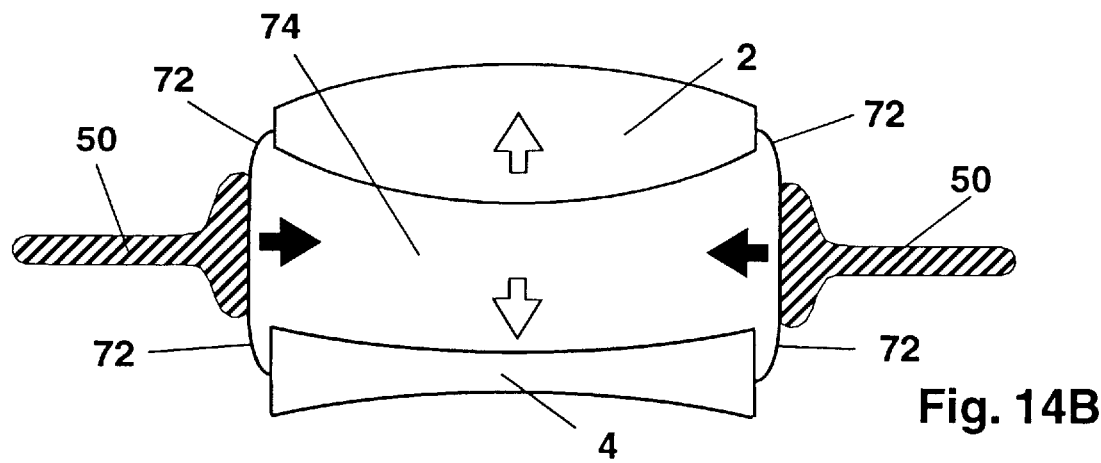

What may be the simplest embodiment of the present invention is to have anterior lens 2 and posterior lens 4 be separated by a moldable liquid filled space 74. This embodiment is shown in FIGS. 14A and 14B. In this embodiment the volume between anterior lens 2 and posterior lens 4 is enclosed in a flexible membrane 72. In this embodiment haptics 50 have been shaped so as to have broad plates which makes it possible for them to exert pressure onto the flexible membrane over relative large areas.

In FIG. 14B is shown the case where haptics 50 have been displaced inward as indicated with filled arrows. This displacement causes liquid filled space 74 to expand in the anterior-posterior direction, as indicated with open arrows, which causes the separation between anterior lens 2 and posterior lens 4 to increase.

OPERATION

The present invention is aimed at simultaneously achieving two goals:

The first goal of the present invention is to enable the lens designer to select the amount of gain relatively freely. By "gain" is meant the amount of change in optical power resulting from a given change in relative position. By "high gain" is meant that small changes in position generate large changes in optical power. Of particular importance is to be able to obtain high gain. The first goal is therefore to enable the lens designer to select the gain relatively freely, including enable the lens designer to select high gain.

The second goal of the present invention is to enable the lens designer to select the amount of overall power of the intraocular lens system relatively independently of the gain.

The principle for achieving the first goal of selecting the amount of gain can be illustrated by considering the idealized case of two thin lenses, in which one lens has positive power and the other has negative power. The power (i.e. the inverse of the focal length) of such a system is described by the formula:

$$1/f = 1/f_a + 1/f_b - t/(f_a f_b),$$

where f denotes the focal length of the overall system (i.e. power=1/f), $f_a$ and $f_b$ represent the focal lengths of the two lenses making up the system and t denotes the distance between the two lenses. As can be seen from this formula, when t moves toward 0, 1/f converges toward $1/f_a + 1/f_b$. That is to say, when the two lenses move toward each other the power of the combined system converges toward the sum of the powers of the two components.

Solving the above equation for f gives the following expression for f:

$$f = (f_a f_b)/(-t + f_a + f_b).$$

From this equation we see that f is equal to infinity if t=0 and $f_a = -f_b$. The derivative of f as a function of t is:

$$df/dt = (f_a f_b)/(f_a + f_b - t)^2.$$

If we then set $f_b = -f_a$ this expression becomes:

$$df/dt = -f_a^2/(-t)^2.$$

This expression means that df/dt will be very large when t is small. That is to say, very small changes in the distance between the lenses will give very large changes in focal length. The amount of change in focal length per unit change in distance depends on the power of the two lenses. These considerations show how it may be possible, in theory at least, to select the gain of an adjustable lens.

With regard to the overall power of the lens system, the above considerations were all made under the assumption that there were one positive lens and one negative lens of equal absolute power (i.e. $f_a = -f_b$). In such a system the overall power is equal to 0 (f=infinity) when the distance between them is 0. That is to say, such a system will create changes in power over a range of powers near zero. An accommodating intraocular lens will have to have an overall power of about 20 diopters (i.e. f=50 mm). This means that positive lens power needs to be added to the system. This additional power could be obtained by adding a separate third lens to the system. Alternatively, it could be obtained by making the positive lens have larger positive power than the negative lens has negative power.

Unfortunately, making the two lenses have unequal power may limit the ability to freely determine the gain of the system (as it was described above). In this context it should also be kept in mind that in practice the lenses will have finite thicknesses. There will therefore be a limit as to how close together the two lenses may be placed. The examples based on thin lenses should therefore only be taken as examples of the underlying principles. The actual performance of a system based on the present principles will have to be determined by ray tracing. In this case one also needs to take account of the fact that an accommodating intraocular lens system will be inside the eye and be located at a place where the rays are converging due to the refracting effect of the cornea. Computer simulated ray tracing indicates that while such factors (i.e. factors such as convergence of the light, the thickness of the lenses and the need for additional power) place restrictions on the freedom to select the gain independently of the overall power, they do not abolish this freedom. On the contrary, one is left with considerable room to select the gain and the power independently.

For the sake of illustration one may consider the case where the anterior lens is a biconcave positive lens and the posterior lens is a negative lens of which at least the anterior surface is concave. Let us further assume that the posterior surface of the anterior lens and the anterior surface of the posterior lens have the same curvature. That is to say, the curvatures are such that the anterior lens and posterior lens make a perfect fit when the two lenses are pushed up against each other. In this case, simulated ray tracing indicates that the overall power of the lens system will be determined mainly by the curvature of the anterior surface of the anterior lens and by the curvature of the posterior surface of the posterior lens. The gain of the overall system on the other hand will be largely determined by the curvature of the posterior surface of the anterior lens, which is equal to the anterior surface of the posterior lens. Generally, the more curved this surface is (i.e. the shorter the radius of curvature) the higher is the gain of the lens system.

In an intraocular lens based on the present lens system it is envisioned that changes in tension in the ciliary muscle will be able to change the distance between the anterior lens and the posterior lens. This will make it possible for the ciliary muscle to change the power of the intraocular lens and will make it possible for a patient to accommodate. It is assumed that the intraocular lens will be placed in a lens capsule after this capsule has been emptied (FIG. 2). Changes in tension of the ciliary muscle will be transmitted to the lens capsule via the zonules. The changes in tension in the lens capsule will then in turn change the tension exerted onto the haptics. Tension changes in the lens capsule and movements of the haptics will occur substantially in a plane perpendicular to the optical axis. In order for these changes to change the power of the present lens system they will have to be translated into positional changes parallel to the optical axis. FIGS. 3–14 show various ways this can be accomplished.

In the preferred embodiment the positive lens will be the anterior lens and the negative lens will be the posterior lens. However, the reverse order also may be used. The formula for the combined power of two thin lenses does not differentiate these two conditions (except for a change in sign).

Because the lens power of at least one of the two lenses may be rather large, it may be desirable to select the shapes and the optical materials for the two lenses so as to minimize the effects of aberrations.

It may also be desirable to be able to compress the intraocular lens at the time of insertion so as to allow the intraocular lens to be inserted into an eye through a small incision. An alternative strategy would be to insert the component parts of the intraocular lens separately and to assemble them once they have been brought inside the eye.

One embodiment involves attaching skirt 40 to one of the two lenses and cylindrical ring 46 to the other lens. This arrangement serves to ensure that the two lenses remain aligned as they move toward and away from each other. In this embodiment, in order to facilitate movement, it would most likely be desirable to have openings through skirt 40 and cylindrical ring 46 so as to allow aqueous to flow freely between the surrounding space and the space inside skirt 40 and cylindrical ring 46. For the sake of clarity and because they do not directly relate to the basic operation of the lens system these openings have not been shown in the drawings.

Whereas the main application for the present lens system is for use in an accommodating intraocular lens, the lens system also would be well suited as the basis for an adjustable fixed focus intraocular lens. When implanting an intraocular lens it is often difficult to select the power of the intraocular lens so as to obtain the correct lens power for generating sharp retinal images. It would therefore represent a major advantage to be able to adjust the power of the intraocular lens after it has been implanted in the eye. The lens system of the present invention has a decided advantage in this respect in that it makes it possible to make substantial adjustments in lens power for small changes in position. In order to achieve this goal it would be necessary to provide means, involving steps such as, for example., the shining of a laser into the eye, whereby the separation between the anterior lens 2 and posterior lens 4 may be adjusted from outside the eye without the need for invasive procedures.

CONCLUSION, RAMIFICATION AND SCOPE

Accordingly, the reader will see that the intraocular lens system of this invention can be used to restore accommodation in a human eye. Furthermore this intraocular lens system has the advantages that it can be fashioned so as to have high gain, thus allowing large changes in optical power to be generated with small changes in the position of the optical elements.

it makes it possible for the gain to be selected relatively independently of the overall power of the lens system.

it allows for a number of embodiments whereby the changes in ciliary muscle tension can be transmitted to the lens system where they can be translated into changes in optical power.

it is consistent with conventional placement of intraocular lenses inside the lens capsule after the capsule has been emptied in the course of extracapsular cataract extraction.

it is well suited as the basis for an adjustable fixed focus intraocular lens the power of which may be adjusted after the intraocular lens has been placed in the eye.

Although the description above contains many specifics, these should not be construed as limiting the scope of the invention but as merely providing illustrations of some of the presently preferred embodiments of this invention. The scope of the invention should be determined by the appended claims and their legal equivalents, rather than by the examples given.

I claim:

1. A lens system for implantation in an eye, said lens system comprising:

(a) one positive lens, (b) one negative lens, (c) adjustment means whereby change s in the ciliary muscle can alter the distance between said positive lens and said negative lens, whereby the overall optical power of said lens system may be adjusted.

2. An intraocular lens system as described in claim 1 in which said positive lens and said negative lens substantially retain their individual shapes during the displacement brought about by activation of said adjustment means.

3. An intraocular lens system as described in claim 1 in which said positive lens and said negative lens each individually substantially retain their individual optical powers during the displacement caused by the activation of said adjustment means.

4. A lens system for implantation in an eye, said lens system comprising:
   (a) one positive lens,
   (b) one negative lens,
   (c) adjustment means whereby increased tension in the ciliary muscle will increase the distance between said positive lens and said negative lens,
whereby the overall optical power of said lens system will be increased.

5. An intraocular lens system as described in claim 4 in which said positive lens and said negative lens each substantially retains its shape during the displacement caused by the activation of said adjustment means.

6. An intraocular lens system as described in claim 4 in which said positive lens and said negative lens each substantially retains its optical power during the displacement caused by the activation of said adjustment means.

7. A method for restoring accommodation in an eye, said method comprising:
   (a) providing an intraocular lens system having:
      (1) one positive lens,
      (2) one negative lens,
      (3) adjustment means whereby changes in the ciliary muscle can cause the distance between said positive lens and said negative lens to be altered,
   (b) inserting said lens system in an eye,
   (c) positioning said lens system inside the eye in such a manner that changes in the ciliary muscle will be transmitted to said adjustment means,
whereby changes in the tension in the ciliary muscle will effect changes in the overall optical power of said lens system.

8. A method for restoring accommodation as described in claim 7, in which said lens system has been deformed in order to facilitate the inserting of said lens system into the eye.

9. A method for restoring accommodation as described in claim 7, in which said lens system has been disassembled into a plurality of parts, each of said parts is introduced individually into the eye in a separate step, and said lens system is reassembled from said parts inside the eye.

* * * * *

UNITED STATES PATENT AND TRADEMARK OFFICE
CERTIFICATE OF CORRECTION

PATENT NO.    : 6,464,725 B2
DATED         : October 15, 2002
INVENTOR(S)   : Bernt Christian Skotton It is certified that error appears in the above-identified patent and that said Letters Patent is hereby corrected as shown below:

<u>Title page,</u>
Item [12], "Skotton" should read -- Skottun --
Item [76], "Bernt Christian Skotton" should read -- Bernt Christian Skottun --

Signed and Sealed this

Sixth Day of May, 2003

JAMES E. ROGAN
*Director of the United States Patent and Trademark Office*